(12) United States Patent
Monroe et al.

(10) Patent No.: US 11,090,408 B2
(45) Date of Patent: Aug. 17, 2021

(54) ANTIMICROBIAL SHAPE MEMORY POLYMERS

(71) Applicant: THE TEXAS A&M UNIVERSITY SYSTEM, College Station, TX (US)

(72) Inventors: Mary Beth Monroe, College Station, TX (US); Duncan J. Maitland, College Station, TX (US); Andrew Weems, Johnson City, TN (US); Brandis Keller, Bryan, TX (US); Grace Fletcher, Houston, TX (US)

(73) Assignee: THE TEXAS A&M UNIVERSITY SYSTEM, College Station, TX (US)

( * ) Notice: Subject to any disclaimer, the term of this patent is extended or adjusted under 35 U.S.C. 154(b) by 0 days.

(21) Appl. No.: 16/466,073

(22) PCT Filed: Dec. 6, 2017

(86) PCT No.: PCT/US2017/064852
§ 371 (c)(1),
(2) Date: Jun. 3, 2019

(87) PCT Pub. No.: WO2018/106775
PCT Pub. Date: Jun. 14, 2018

(65) Prior Publication Data
US 2019/0282726 A1    Sep. 19, 2019

Related U.S. Application Data

(60) Provisional application No. 62/430,620, filed on Dec. 6, 2016.

(51) Int. Cl.
| | | |
|---|---|---|
| *A61L 24/00* | (2006.01) | |
| *A61L 24/04* | (2006.01) | |
| *C08G 18/10* | (2006.01) | |
| *C08G 18/73* | (2006.01) | |
| *C08G 18/83* | (2006.01) | |
| *C08J 9/36* | (2006.01) | |
| *A61L 15/26* | (2006.01) | |
| *A61L 27/50* | (2006.01) | |
| *A61L 31/14* | (2006.01) | |
| *A61L 31/16* | (2006.01) | |
| *A61L 15/46* | (2006.01) | |
| *A61L 27/18* | (2006.01) | |
| *A61L 27/56* | (2006.01) | |
| *A61L 15/42* | (2006.01) | |
| *A61L 31/06* | (2006.01) | |
| *A61L 27/54* | (2006.01) | |

(52) U.S. Cl.
CPC .......... *A61L 24/0015* (2013.01); *A61L 15/26* (2013.01); *A61L 15/42* (2013.01); *A61L 15/425* (2013.01); *A61L 15/46* (2013.01); *A61L 24/001* (2013.01); *A61L 24/0036* (2013.01); *A61L 24/046* (2013.01); *A61L 27/18* (2013.01); *A61L 27/50* (2013.01); *A61L 27/54* (2013.01); *A61L 27/56* (2013.01); *A61L 31/06* (2013.01); *A61L 31/14* (2013.01); *A61L 31/146* (2013.01); *A61L 31/16* (2013.01); *C08G 18/10* (2013.01); *C08G 18/73* (2013.01); *C08G 18/831* (2013.01); *C08J 9/36* (2013.01); *A61L 2300/216* (2013.01); *A61L 2300/404* (2013.01); *A61L 2400/04* (2013.01); *A61L 2400/16* (2013.01); *C08G 2280/00* (2013.01); *C08J 2207/10* (2013.01); *C08J 2375/04* (2013.01)

(58) Field of Classification Search
CPC .... A61L 27/56; A61L 24/001; A61L 24/0036; A61L 27/18; A61L 24/0015; A61L 31/146; A61L 31/06; A61L 27/54; A61L 15/26; A61L 27/50; A61L 15/425; A61L 15/42; A61L 24/046; A61L 15/46; A61L 15/44; A61L 31/16; A61L 31/14; A61L 2400/04; A61L 2300/216; A61L 2300/404; A61L 2300/442; A61L 2430/02; A61L 2400/16; A61L 2300/104; A61L 2300/21; A61L 2430/36; C08G 18/73; C08G 18/831; C08G 18/10; C08G 2280/00; C08J 9/36; C08J 2375/04; C08J 2207/10; C08L 75/04
See application file for complete search history.

(56) References Cited

U.S. PATENT DOCUMENTS

| | | |
|---|---|---|
| 5,607,741 A | 3/1997 | Zimmerman et al. |
| 6,294,186 B1 | 9/2001 | Beerse et al. |
| 7,714,183 B2 | 5/2010 | Caskey |

(Continued)

FOREIGN PATENT DOCUMENTS

| | | |
|---|---|---|
| CA | 2896315 | 7/2014 |
| CN | 1282216 A | 1/2001 |

(Continued)

OTHER PUBLICATIONS

English translation of WO-2006102842-A1, translated from Google Patents. Retrieved online Jul. 20, 2020 . (Year: 2020).*
M. Sova, "Antioxidant and Antimicrobial Activities of Cinnamic Acid Derivatives," Mini-Reviews in Medicinal Chemistry, 2012, 20 pages total.
Juan David Guzman, "Natural Cinnamic Acids, Synthetic Derivatives and Hybrids with Antimicrobial Activity," Molecules Journal, 2014, 58 pages.

(Continued)

*Primary Examiner* — Doan T Phan
(74) *Attorney, Agent, or Firm* — Trop, Pruner & Hu, P.C.

(57) ABSTRACT

An embodiment includes a system comprising a thermoset polyurethane shape memory polymer (SMP) foam that includes at least one antimicrobial agent. The antimicrobial agent may include at least one phenolic acid that is a pendent group chemically bonded to a polyurethane polymer chain of the SMP foam. Other embodiments are described herein.

4 Claims, 9 Drawing Sheets

(56) References Cited

U.S. PATENT DOCUMENTS

| | | | |
|---|---|---|---|
| 2006/0257629 A1* | 11/2006 | Lendlein | A61L 27/50 |
| | | | 428/195.1 |
| 2012/0059117 A1 | 3/2012 | Codina et al. | |
| 2013/0317541 A1* | 11/2013 | Singhal | A61B 17/0057 |
| | | | 606/213 |
| 2016/0270961 A1* | 9/2016 | Maitland | A61L 15/26 |

FOREIGN PATENT DOCUMENTS

| | | | |
|---|---|---|---|
| CN | 101161299 A | 4/2008 | |
| CN | 101428156 A | 5/2009 | |
| CN | 101528278 A | 9/2009 | |
| CN | 101588715 A | 11/2009 | |
| CN | 101817746 A | 9/2010 | |
| CN | 104 744 664 | 7/2015 | |
| EP | 3031597 A1 * | 6/2016 | C08G 18/797 |
| WO | 2002087644 | 11/2002 | |
| WO | WO2004063088 | 7/2004 | |
| WO | 2006083628 A2 | 8/2006 | |
| WO | WO-2006102842 A1 * | 10/2006 | A61F 5/01 |
| WO | 2010010399 | 1/2010 | |
| WO | 2016007776 | 1/2016 | |
| WO | 2016149070 | 9/2016 | |
| WO | 2018102779 | 6/2018 | |

OTHER PUBLICATIONS

Chanwitheesuk, et al., "Antimicrobial gallic acid from Caesalpinia mimosoides Lamk", Food Chemistry, 2007, pp. 1044-1048, vol. 100, Issue 3.

Chung, et al., "Antimicrobial nanostructured polyurethane scaffolds", Advances in Polyurethane Biomaterials, 1st edition, Feb. 16, 2016, pp. 503-521, Elsevier Science & Technology.

International Searching Authority, "Notification of Transmittal of the International Search Report and the Written Opinion of the International Searching Authority," dated Mar. 22, 2018, in International application No. PCT/US2017/064852.

Mary Beth Monroe, Ph.D., "Antimicrobial Shape Memory Polymer Foam Hemostats," Dec. 7, 2016, 26 pages.

International Searching Authority, "International Preliminary Report on Patentability" dated Jun. 11, 2019, in International application No. PCT/US2017/064852.

Akers, et al., "Biofilms and persistent wound infections in United States military trauma patients: a case-control analysis", 2014, 11 pages, BMC Infectious Diseases.

Boyle, et al., "In vitro and in vivo evaluation of a shape memory polymer foam-over-wire embolization device delivered in saccular aneurysm models", Feb. 24, 2015, nine pages, Society for Biomaterials.

Chaturvedi, et al., "Hydrophobically modified chitosan gauze: a novel topical hemostat", Jan. 2017, pp. 45-52, vol. 207, Journal of Surgical Research.

Cohen, "Epidemiology of Drug Resistance: Implications for a Post-Antimicrobial Era", Aug. 21, 1992, pp. 1050-1055, vol. 257, Issue 5073, Science Magazine.

Dayan, et al., "Complications Associated with Prolonged Tourniquet Application on the Battlefield", Jan. 2008, pp. 63-66, vol. 173, Military Medicine.

Eastridge, et al., "Death on the battlefield (2001-2011): Implications for the future of combat casualty care", Dec. 2012, seven pages, Journal Trauma Acute Care Surgical, Lippincott Williams & Wilkins.

Eastridge, et al., "Died of Wounds on the Battlefield: Causation and Implications for Improving Combat Casualty Care", Jul. 2011, vol. 71, No. 1, The Journal of Trauma Injury, Infection, and Critical Care.

Ellson, et al., "Tunable thiol-epoxy shape memory polymer foams", 2015, 12 pages, Smart Materials and Structures, IOP Publishing, Ltd.

Fiuza, et al., "Phenolic acid derivatives with potential anticancer properties—a structure-activity relationship study. Part 1: Methyl, propyl and octyl esters of caffeic and gallic acids", 2004, nine pages, Bioorganic & Medicinal Chemistry 12, Elsevier Ltd.

Monroe, et al., "Multifunctional Shape-Memory Polymer Foams with Bioinspired Antimicrobials", 2017, pp. 1-11, vol. 18, Wiley-VCH Verlag GmbH & Co. KGaA, Weinheim.

Horn, et al., "Comparison of shape memory polymer foam versus bare metal coil treatments in an in vivo porcine sidewall aneurysm model", Journal of Biomedical Materials Research B: Applied Biomaterials, Oct. 2017, pp. 1892-1905, vol. 105b, issue 7.

Hsu, et al., "Multifunctional Self-Assembled Films for Rapid Hemostat and Sustained Anti-infective Delivery", ACS Biomatenals Science & Engineering, 2015, pp. 148-156, vol. 1, American Chemical Society.

Kauvar, et al., "Impact of Hemorrhage on Trauma Outcome: An Overview of Epidemiology, Clinical Presentations, and Therapeutic Considerations", The Journal of Trauma Injury, Infection, and Critical Care, 2006, nine pages, vol. 60, No. 6, Lippincott Williams & Wilkins.

Kheirbek, et al., "Hypothermia in bleeding trauma: a friend or a foe?", Scandinavian Journal of Trauma, Resuscitation and Emergency Medicine, Dec. 23, 2009, 15 pages.

Kotwal, et al., "Eliminating Preventable Death on the Battlefield", Archive of Surgery, vol. 146, No. 12, Dec. 2011, American Medical Association.

Kragh, Jr., et al., "Gauze vs XSTAT in wound packing for hemorrhage control", The American Journal of Emergency Medicine, Jul. 2015, vol. 33, Issue 7, pp. 974-976.

Kumar, et al., "Nanofibrous Snake Venom Hemostat", ACS Biomaterial Science Engineering, Oct. 22, 2015, pp. 1300-1305, vol. 1, American Chemical Society.

Landsman, et al., "A shape memory foam composite with enhanced fluid uptake and bactericidal properties as a hemostatic agent", Acta Biomaterialia, 2017, pp. 91-99, vol. 47, Acta Biomaterialia Materialia Inc., Elsevier Ltd.

Lendlein, et al., "Shape-Memory Polymers", Angewandte Chemie International Edition, Jun. 12, 2002, pp. 2034-2057, vol. 41, Issue 12, Wiley-VCH Verlag GmbH.

Merkl, et al., "Antimicrobial and Antioxidant Properties of Phenolic Acids Alkyl Esters", Czech Journal of Food Sciences, Jan. 2010, pp. 275-279, vol. 28, No. 4.

Metcalfe, et al., "Cold hibernated elastic memory foams for endovascular interventions", Biomaterials, vol. 24, 2003, pp. 491-497, Elsevier Science Ltd.

Mueller, et al., "A novel sponge-based wound stasis dressing to treat lethal noncompressible hemorrhage", Journal of Trauma Acute Care Surgical, 2002, six pages, vol. 73, No. 2, Supplement 1.

Murray, et al., "Prevention and Management of Infections Associated With Combat-Related Extremity Injuries", The Journal of Trauma Injury, Infection, and Critical Care, 2008, 13 pages, vol. 64, No. 3.

Narasimhan, et al., "Esters, amides and substituted derivatives of cinnamic acid: synthesis, antimicrobial activity and QSAR investigations", European Journal of Medicinal Chemistry, 2004, pp. 827-834, vol. 39, Elsevier SAS.

Nascimento, et al., "Antibacterial Activity of Plant Extracts and Phytochemicals on Antibiotic-Resistant Bacteria", Brazilian Journal of Microbiology, 2000, pp. 247-256, vol. 31.

Nash, et al., "Cold Plasma Reticulation of Shape Memory Embolic Tissue Scaffolds", Marcomolecular Rapid Communications, 2016, pp. 1945-1951, vol. 37.

Nash, et al., "Increased X-ray Visualization of Shape Memory Polymer Foams by Chemical Incorporation of Iodine Motifs", Polymers, Aug. 20, 2017, 16 pages, vol. 9, No. 8, 381, https://doi.org/10.3390/polym9080381.

Natella, et al., "Benzoic and Cinnamic Acid Derivatives as Antioxidants: Structure-Activity Relation", Journal of Agricultural and Food Chemistry, Mar. 17, 1999, pp. 1453-1459, vol. 47, American Chemical Society.

Nathan, et al., "Particulate Release From Nanoparticle-Loaded Shape Memory Polymer Foams", Journal of Medical Devices, Mar. 2017, 9 pages, vol. 11.

"Pendant Group", Wikipedia, last edited on Dec. 21, 2016, one page, https://en.wikipedia.org/wiki/Pendant_group.

(56) References Cited

OTHER PUBLICATIONS

"Prepolymer", Wikipedia, last edited on Dec. 21, 2016, one page, https://en.wikipedia.org/wiki/Prepolymer.

Pusateri, et al., "Advanced Hemostatic Dressing Development Program: Animal Model Selection Criteria and Results of a Study of Nine Hemostatic Dressings in a Model of Severe Large Venous Hemorrhage and Hepatic Injury in Swine", The Journal of Trauma Injury, Infection, and Critical Care, Sep. 2003, pp. 518-526, vol. 55.

Rials, et al., "Engineering Plastics from Lignin. IV. Effect of Crosslink Density on Polyurethane Film Properties—Variation in NCO:OH Ratio", Holzforschung, pp. 191-199, vol. 38.

Rodriguez, et al., "Reticulation of low density shape memory polymer foam with an invivo demonstration of vascular occlusion", Journal of the Mechanical Behavior of Biomedical Materials, 2014, pp. 102-114, vol. 40, Elsevier Ltd.

Rodriguez, et al., "In vivo response to an implanted shape memory polyurethane foam in a porcine aneurysm model", Journal of Biomedical Materials Research, Part A, May 2014, pp. 1231-1242, vol. 102A, Issue 5, Wiley Periodicals, Inc.

Zhang, et al., "A bioactive "self-fitting" shape memory polymer scaffold with potential to treat cranio-maxillo facial bone defects", Acta Biomaterialia, 2014, pp. 4597-4605, vol. 10, Elsevier Ltd.

Anabela Borges, et al., "Biofouling: The Journal of Bioadhesion and Biofilm Research," CECAV—Veterinary and Animal Science Research Center, Veterinary Science Department, Published online: Jul. 24, 2012, 14 pages.

P. C. Molan, et al., "Clinical usage of honey as a wound dressing: an update," Journal of Wound Care, vol. 13, No. 9, Oct. 2004, 4 pages.

Teodoro, et al., "Potential Use of Phenolic Acids as Anti-Candida Agents: A Review," Dec. 21, 2015, 11 pages.

H.A.L. Wandan, "Causes of the Antimicrobial Activity of Honey," 1998, 6 pages.

European Patent Office, Supplementary European Search Report dated Jul. 30, 2020 in European patent application No. 17 877 973.2, 12 pages total.

Database Medline, Perni Stefano, et al., "Antimicrobial Properties of Light-Activated Polyurethane Containing Indocyanine Green," Journal of Biomaterials Applications, Jan. 2011, 2 pages total.

Gi Byoung Hwang, et al., "White Light-Activated Antimicrobial Surfaces: Effect of Nanoparticles Type on Activity," Journal of Materials Chemistry, vol. 4, No. 12, Jan. 1, 2016, 9 pages total.

Chinese Patent Office, Office Action dated Apr. 27, 2021 in Chinese Patent Application No. 201780075839.3 (27 pages).

\* cited by examiner

| Phenolic Acid | Incorporation Mechanism | Concentration in Foam (mol%) |
|---|---|---|
| Cinnamic Acid | Esterification with HPED | 10, 20, and 30 |
| | Direct Incorporation | 10, 20, and 30 |
| Gentisic Acid | Esterification with HPED | 10, 20, and 30 |
| | Direct Incorporation | 10, 20, and 30 |
| Benzoic Acid | Esterification with HPED | 10, 20, and 30 |
| | Direct Incorporation | 10, 20, and 30 |

FIGURE 3

| Foam Formulation | Pore Size [μm] | Density [g/cm³] |
|---|---|---|
| Control | 960 ± 160 | 0.027 ± 0.002 |
| CA | 1100 ± 150 | 0.023 ± 0.001 |
| CAOH | 1050 ± 150 | 0.018 ± 0.001 |

FIGURE 4

| Foam Formulation | Dry Glass Transition Temperature (Tg, °C) | Wet Glass Transition Temperature (Tg, °C) | Volume Recovery (%) | Volume Expansion (cm³) |
|---|---|---|---|---|
| Control | 67 ± 1 | 35 ± 2 | 100 (target) | 25 (target) |
| CA | 69 ± 1 | 26 ± 3 | 92.1 ± 0.2 | 27.1 ± 0.9 |
| CAOH | 67 ± 1 | 23 ± 1 | 103.5 ± 0.2 | 25.3 ± 1.6 |

| Formulation Name | NCO Equivalents | | OH Equivalents | | | |
| --- | --- | --- | --- | --- | --- | --- |
| | HDI | HPED | TEA | CA | HCA |
| Control | 100% | 70% | 30% | -- | -- |
| 10% CA | 100% | 70% | 20% | 10% | -- |
| 10% HCA | 100% | 70% | 20% | -- | 10% |
| 20% HCA | 100% | 70% | 10% | -- | 20% |
| 30% HCA | 100% | 70% | -- | -- | 30% |

FIGURE 12

ANTIMICROBIAL SHAPE MEMORY POLYMERS

CROSS-REFERENCE TO RELATED APPLICATION

This application claims priority to U.S. Provisional Patent Application No. 62/430,620 filed on Dec. 6, 2016 and entitled "Antimicrobial Shape Memory Polymers", the content of which is hereby incorporated by reference.

TECHNICAL FIELD

Embodiments of the invention are in the field of shape memory polymer medical devices.

BACKGROUND

Hemorrhage is the leading cause of potentially preventable death on the battlefield. The current standard of field care is to utilize gauze in combination with tourniquets; however, these treatments are insufficient for up to 80% of wounds. Furthermore, tourniquets only serve as temporary measures against blood loss, as tourniquet use beyond ~4-6 hours is associated with limb damage and loss. An improved hemostat material could enable earlier tourniquet removal before patients can receive treatment at a fixed facility.

The current standard of care on the battlefield involves the use of a broad spectrum antibiotic regimen in combination with frequent dressing changes to prevent bacterial and fungal infections; however, rising concerns over antibiotic resistance requires the use of alternative treatment methods, and dressing changes are not always feasible during battle.

BRIEF DESCRIPTION OF THE DRAWINGS

Features and advantages of embodiments of the present invention will become apparent from the appended claims, the following detailed description of one or more example embodiments, and the corresponding figures. Where considered appropriate, reference labels have been repeated among the figures to indicate corresponding or analogous elements.

FIG. 2(A) Transmission Fourier transform infrared (FTIR) spectra of HCA compared to HPED and CA, FIG. 2(B) Nuclear magnetic resonance (NMR) spectra of HCA, FIG. 2(C) Attenuate total reflectance (ATR)-FTIR spectra of control, CA, and HCA foams.

FIG. 3. Phenolic acid-containing foam compositions

FIG. 4. Pore size and density of SMP foams synthesized with CA and CAOH monomers.

FIG. 7(A) Density, FIG. 7(B) Pore size (axial and transverse foaming directions) and isotropicity (ratio between pore sizes in the axial and transverse foaming directions), and FIG. 7(C) Representative scanning electron micrographs in the axial and transverse foaming directions. Scale bar applies to all images.

FIG. 8(A) Dry and wet glass transition temperatures (Tg), FIG. 8(B) Volume recovery profile in 37° C. water, FIG. 8(C) Time to 100% volume recovery in 37° C. water.

FIG. 12. Antimicrobial SMP compositions. NCO: Isocyanate; OH: Hydroxyl.

DETAILED DESCRIPTION

Figure 1:
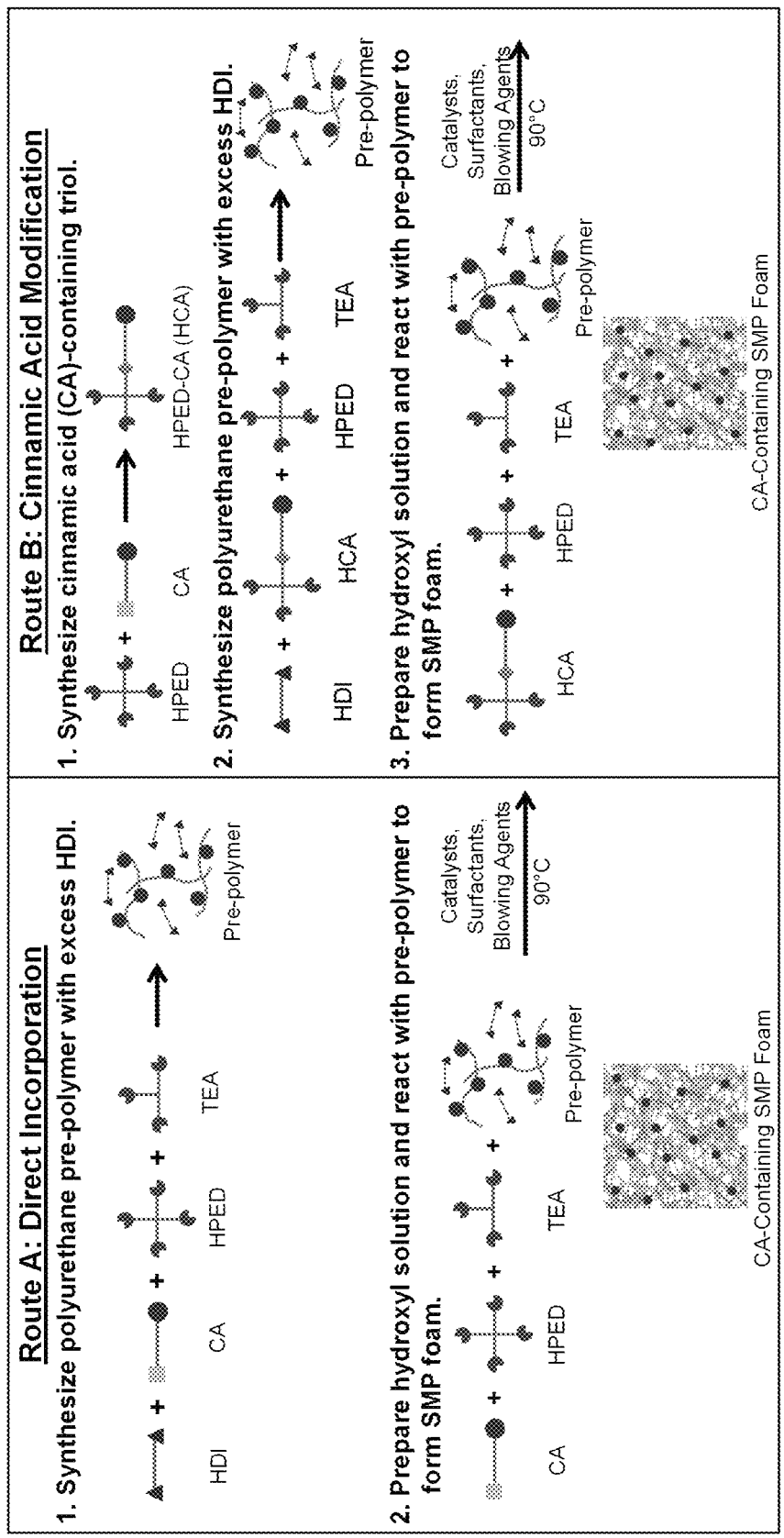
FIG. 1. Schematic representation of cinnamic acid (CA) incorporation into shape memory polymer (SMP) foams. Route A: In an embodiment a pre-polymer was prepared with CA, hydroxypropyl ethylene diamine (HPED), triethanolamine (TEA), and excess hexamethylene diisocyanate (HDI). The pre-polymer was reacted with the remaining CA, HPED, and TEA in the presence of catalysts, surfactants, and blowing agents while heating to form a CA-containing SMP foam. Route B: In an embodiment the carboxylic acid group on CA was esterified with a hydroxyl group on HPED to form HCA. Then, HCA was used as a foaming monomer in place of CA in the same method utilized for Route A to form a CA-containing SMP foam.

"An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner.

Below various embodiments are addressed. Embodiments are first addressed in the section entitled "OVERVIEW OF AN EMBODIMENT". Embodiments are then further addressed in sections entitled "HIGH LEVEL DESCRIPTION OF EMBODIMENTS" and "MORE DETAILED DESCRIPTION OF EMBODIMENTS."

Overview of an Embodiment or Embodiments

There are numerous and growing concerns in the medical community over antibiotic-resistant bacteria that result in infections that are very difficult to treat. To address these concerns, an embodiment includes the incorporation of antimicrobials into shape memory polymers (SMPs). SMPs are highly valuable materials that may be employed in a range of medical devices or other devices. An embodiment incorporates non-drug-based antimicrobial agents (e.g., phenolic acids from honey, fluorescent dyes, silver, or peroxide-producing compounds) into SMPs. The presence of these antimicrobial agents provides localized infection prevention around SMP-based devices. An embodiment provides that antimicrobial properties are introduced by including small antimicrobial or antimicrobial-producing agents in the polymer synthesis to chemically or physically incorporate antimicrobials into the polymer network.

Thus, embodiments include SMP-based medical devices with infection resistance. Embodiments include antimicrobial SMPs to be employed in a wide range of medical devices including, but not limited to, endovascular medical devices, wound dressings, hemostat materials, lung puncture sealants, and/or bone grafts. In an embodiment SMP medical devices with incorporated antimicrobials work in conjunction with oral antibiotics to reduce local infection risks in damaged tissue.

Such embodiments are important for various reasons. For example, these antimicrobial SMP-based medical devices meet large clinical needs in treatment and infection prevention because infections acquired at the point of injury and/or in the hospital environment are a significant source of health care costs and contribute to patient morbidity and mortality rates. By delivering antimicrobial agents directly to the source of wounding or implantation, these infections and their complications are reduced, particularly with the use of broad-spectrum antimicrobials that are effective against drug-resistant bacteria strains. SMP medical devices can be easily delivered into small and/or irregularly-shaped defect sites. Thus, antimicrobial SMPs provide new treatment options with reduced infection risks.

Such embodiments are novel for various reasons. For example, the incorporation of non-drug-based antimicrobial agents directly into SMPs and the subsequent fabrication of devices with complex architectures are novel. A point of novelty includes incorporating non-drug small antimicrobial molecules (e.g., phenolic acids and fluorescent dyes) into a SM polymer foam system to enable delivery in a medical device.

Further regarding the antimicrobial molecules, an embodiment includes phenolic acids (PAs). Bees produce plant-derived PAs in their honey, which protect hives against microbes and viruses. PAs exhibit broad antimicrobial properties, and have been shown to be effective against multidrug resistant organisms (MDROs). For example, antibiotic-resistant bacteria that were obtained from hospitals (*Enterobacter aerogenes, Escherichia coli,* and *Staphylococcus aureus*) were susceptible to the PA cinnamic acid. Similarly, two other Pas (ferulic and gallic acids) reduced biofilm activity >70% for four human pathogenic bacteria (*Escherichia coli, Pseudomonas aeruginosa, Staphylococcus aureus,* and *Listeria monocytogenes*).

As an alternative to PAs, embodiments use a number of fluorescent molecules that have antimicrobial activity and chemistries that enable their incorporation into SMPs. An additional embodiment incorporates monomers that naturally produce peroxides in the presence of water.

As an additional advantage, the technique of utilizing antimicrobials as monomers enables fine-tuning of SMP properties using standard variables, such as hydrophobicity and crosslink density. This property expands the potential applications of antimicrobial SMPs, as they can be processed and tuned to match a range of tissue types.

Another embodiment uses an antimicrobial SMP that includes the physical incorporation of antimicrobial particles, such as silver nanoparticles. Nanoparticle fillers improve SMP scaffold mechanical properties. Thus, the addition of silver nanoparticles both enhances SMP mechanical integrity and provides antimicrobial resistance.

There are still further advantages with embodiments. Previous work (Landsman, et al. Acta Biomaterialia (2016)) included SMP foams integrated with iodine-containing hydrogels. While these iodine "sponges" also provide an option for antimicrobial SMP system, the antimicrobial properties are fully dependent upon the hydrogel component, with no antimicrobials directly incorporated into the SMP. In contrast, an embodiment utilizes a SMP-only scaffold with varied mechanisms of incorporating antimicrobials.

Various embodiments of antimicrobial SMP foams are fabricated by a number of routes.

ROUTE 1: Functionalize an antimicrobial or peroxide-producing monomer with reactive hydroxyl or amine groups to enable their incorporation into the polyurethane. Briefly, the carboxylic acid of a phenolic acid is esterified with a foaming polyol (e.g., N,N,N',N'-tetrakis(2-hydroxypropyl) ethylenediamine (HPED) or triethanolamine) in an appropriate solvent with esterification catalysts (e.g., dicyclohexylcarbodiimide (DCC) and dimethylaminopyridine (DMAP)). The reaction is filtered and washed to remove byproducts and residual catalysts, and the final product is isolated by rotary evaporation. This method is appropriate for use with any antimicrobial agent that has a carboxylic acid group. The final product is utilized as a polyol in SMP synthesis with other polyols (e.g., HPED and/or TEA) and diisocyanates (e.g. hexamethylene diisocyanate, trimethyl hexamethylene diisocyanate, and/or isophorone diisocyanate).

ROUTE 2: Direct chemical incorporation into SMP. Briefly, any antimicrobial or peroxide-producing monomer with a reactive group (e.g., carboxylic acid, hydroxyl, or primary or secondary amine) is reacted with polyols (e.g., HPED and/or TEA) and diisocyanates (e.g., hexamethylene diisocyanate, trimethyl hexamethylene diisocyanate, and/or isophorone diisocyanate) to form a polyurethane SMP.

ROUTE 3: Direct physical incorporation into SMP. Briefly, any antimicrobial or peroxide-producing monomer or particle (nano or micro-scale) is mixed with SMP monomers (e.g., polyols (e.g., HPED and/or TEA) and diisocyanates (e.g. hexamethylene diisocyanate, trimethyl hexamethylene diisocyanate, and/or isophorone diisocyanate)) prior to the crosslinking reaction to result in a SMP network with physically incorporated antimicrobials. Thus, the SMP foam is crosslinked around the antimicrobial or peroxide-producing monomer or particle. In an embodiment, the iso or "B" side and "poly" or "A" side of the polymer chain are crosslinked around the antimicrobial or peroxide-producing monomer or particle.

Generally, a SMP network includes switch units or segments and netpoints or domains. The netpoints determine the permanent shape of the polymer network. In an embodiment the antimicrobial agent is a physically crosslinked netpoint. With the antimicrobial agent the SMP foam comprises a composite and is therefore stronger in response to the inclusion of the antimicrobial agent.

Any of the above routes are utilized with bulk or porous SMPs. After synthesis, the material is cut, cleaned, processed, and incorporated into a medical device.

Embodiments include PAs that have been successfully modified with HPED and utilized in SMP foam and bulk film synthesis. The PA-containing SMPs have similar thermal transition temperatures to controls and demonstrate shape memory properties. The PA-containing SMPs demonstrate effective reduction in *Escherichia coli* growth in comparison to controls.

Various SMP foams have been discussed. Embodiments include polyurethane SMP foams synthesized by some combination of: (a) Hexamethylene diisocyanate, trimethyl hexamethylene diisocyanate, isophorone diisocyanate, triethanolamine, diethanolamine, butane diol, butyne diol, N,N,N', N' tetrakis (hydroxyl propylene) ethylenediamine, and (b) an antimicrobial agent which could include, but is not limited to: phenolic acids (e.g. cinnamic acid, benzoic acid, gentisic acid, 4-hydroxy benzoic acid, p-coumaric acid, vanillic acid, syringic acid, protocatechuic acid, gallic acid, ferulic acid, sinapic acid, caffeic acid), fluorescent dyes (e.g. phloxine B, toluidine blue O, indocyanine green), or metallic particles or metallic nanoparticles (e.g. colloidal silver).

High Level Description of Embodiments

Antimicrobial agents are incorporated into polyurethane shape memory polymers (SMPs), FIG. 1. In some embodiments, incorporated antimicrobials work in conjunction with oral antibiotics to reduce infection risks in implanted SMP-based devices. There are numerous concerns about antibiotic-resistant bacterial strains. To address this issue, antimicrobial phenolic acids (PAs) are utilized in a non-drug approach. Bees produce plant-derived PAs in their honey, which protect hives against microbes and viruses. PAs exhibit broad antimicrobial properties, and have been shown to be effective against multi-drug resistant organisms (MDROs). For example, antibiotic-resistant bacteria that were obtained from hospitals (*Enterobacter aerogenes*, *Escherichia coli*, and *Staphylococcus aureus*) were susceptible to cinnamic acid. A recent review covers the efficacy of a number of PAs, including cinnamic, gentisic, and benzoic acids, against *Candida* infections (planktonic and biofilms, drug susceptible and drug resistant). Furthermore, ferulic and gallic acids reduced biofilm activity >70% for four human pathogenic bacteria (*Escherichia coli*, *Pseudomonas aeruginosa*, *Staphylococcus aureus*, and *Listeria monocytogenes*). By taking a single component of honey (e.g., PA) and utilizing it as a foaming monomer, we harness the benefits of PAs while maintaining a synthetic medical device system.

Study 1.1: Fabricate PA-containing SMP foams. PA (modified and unmodified) antimicrobial efficacy against MDROs is measured to down-select agents prior to foam fabrication. For all agents with acceptable antimicrobial properties, SMP foams are synthesized with varying levels of cinnamic, gentisic, and benzoic acid via (a) prior esterification with foaming polyols to produce a PA-containing polyol (PAOH) and (b) direct incorporation. In an embodiment route (a) requires fewer alterations to foam composition. Prior esterification enhances the antimicrobial properties of PAs. Furthermore, route (a) eliminates/reduces bubble generation from the reaction between carboxylic acids on PAs and isocyanates in the foams to better control foam properties. Route (b) is simpler and less expensive. Thus, in some embodiments foams synthesized via route (b) that meet all success criteria and produce consistent and reliable foams are advantageous.

Methods: PAOH Synthesis: PAOH is synthesized from hydroxypropyl ethylenediamine (HPED) and select PAs (cinnamic acid, gentisic acid, and benzoic acid) via esterification in chloroform (catalyzed by dicyclohexylcarbodiimide (DCC) and dimethylaminopyridine (DMAP)) for 3 hours at room temperature, FIG. 1. The reaction is filtered and washed to remove byproducts and residual catalysts, and the final product is isolated by rotary evaporation. Successful synthesis of PAOH is confirmed using Fourier transform infrared (FTIR) and nuclear magnetic resonance (NMR) spectroscopy.

Figure 2:
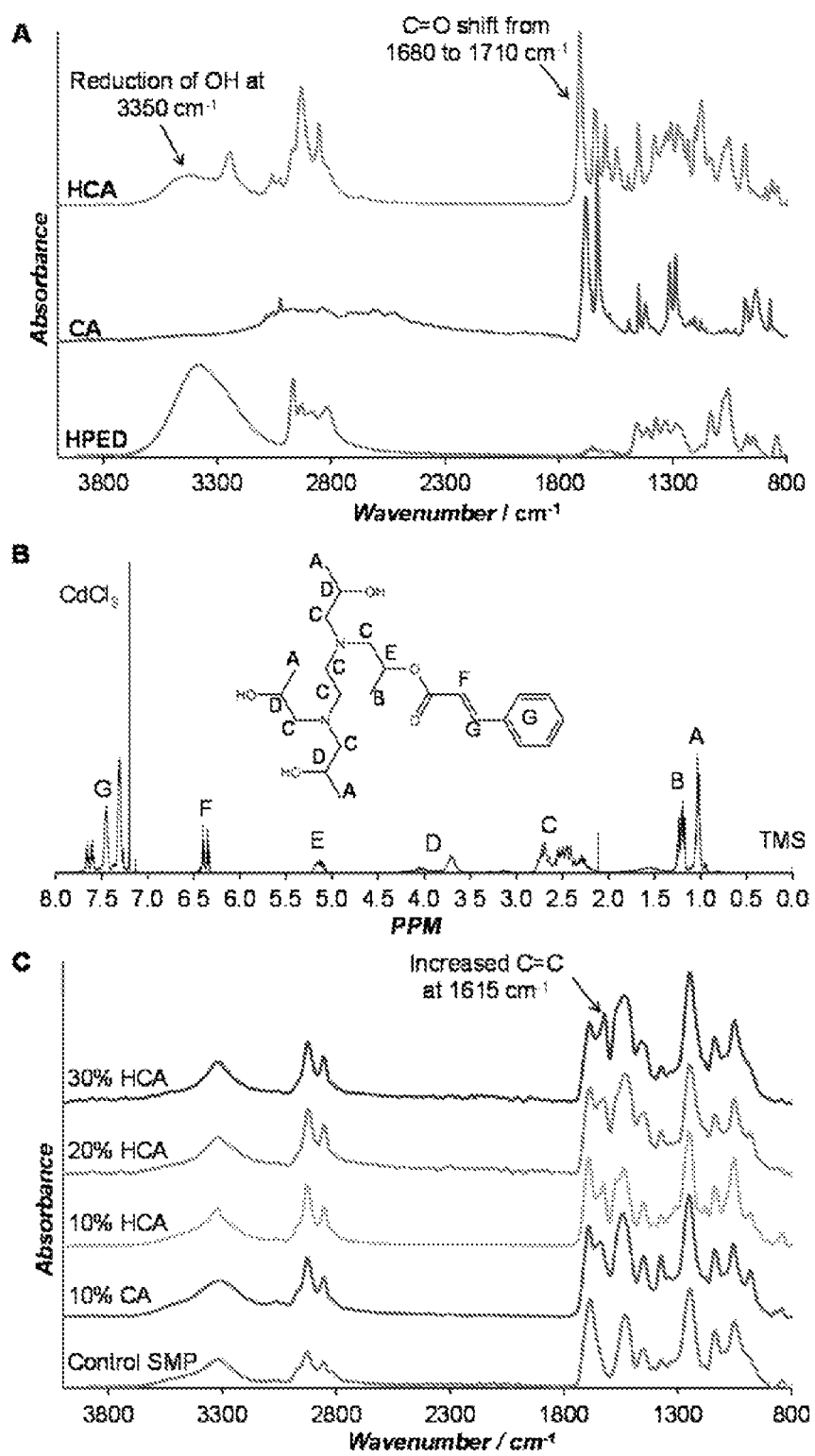
FIG. 2. Spectral confirmation of synthesis of HCA/CA foams.

Results: Cinnamic acid-HPED (CAOH) was successfully synthesized, as indicated by FTIR spectra that show a reduction in hydroxyl groups relative to HPED and formation of ester linkages, FIG. 2.

Foam Synthesis: Because PAs and PAOH derivatives are effective antimicrobials, foams are synthesized with varied amounts of PAOH in combination with HPED and hexamethylene diisocyanate (HDI) as previously described, FIG. 1. Briefly, a polyurethane prepolymer is synthesized using an excess of HDI with PAOH and HPED. The remainder of PAOH and HPED are mixed together and added to the prepolymer at a final molar ratio of 1:1 (isocyanates (HDI): hydroxyls (PAOH and HPED)) in some embodiments. Upon addition of the hydroxyl mix to the prepolymer, catalysts, surfactants, water (chemical blowing agent), and Enovate (physical blowing agent) are added, and the components are mixed until homogenous. The resulting foaming mixture is cured at 90° C. for 20 minutes in an embodiment. In parallel, PA-containing foams are synthesized via direct incorporation of phenolic acids into the polyurethane backbone (reaction between carboxylic acid on PAs and isocyanates in foam), FIG. 3.

Study 1.2: Characterize PA-containing foam structure; mechanical, thermal, and shape memory properties; and cytocompatibility. After a library of PA-containing foams is synthesized, they are characterized to ensure that desirable foam properties are retained. In particular, embodiments of PA-containing foams have thermal transitions at body temperature in aqueous conditions to enable shape change upon application of a bleed, rapid shape recovery (<2 minutes) to enhance wound filling and clotting speed, and high cytocompatibility as an initial indication of their safety. These properties are achieved with a number of the compositions described herein.

Methods: Structure: After incorporation of PAOH and PAs into foams, foam pore size and structure are quantified. Thin samples are cut laterally and longitudinally from each foam, sputter coated in gold, and imaged using scanning electron microscopy (SEM). Pore sizes and strut thicknesses are quantified from SEM images using ImageJ software.

Results: CA and CAOH were successfully incorporated into SMP foams, resulting in low density foams with retained pore sizes of ~1000 µm, FIG. 3.

Thermal Properties: The glass transition temperature (Tg) of control and modified foams are measured using differential scanning calorimetry (DSC) under wet and dry conditions. For dry Tg, a 3-8 mg sample is loaded into an aluminum pan at room temperature, cooled to −40° C. using the DSC, and then heated to 120° C. The sample is cooled and heated again, and Tg is recorded from the second cycle as the inflection point of the thermal transition curve. For wet Tg, 3-8 mg foam samples are submerged in reverse osmosis water at 50° C. for 5 min to allow full plasticization and then pressed dry with laboratory wipes. Samples are weighed and placed in a vented aluminum pan. The DSC is used to cool the samples to −40° C. and heat them to 80° C. The wet Tg (after water plasticization) is determined using the average inflection point of the thermal transition.

Results: CA and CAOH-containing SMP foams exhibited retained dry thermal properties relative to control, FIG. 4. The wet glass transition temperatures were reduced relative to the control, but maintained below body temperature to enable actuation upon implantation.

Shape Memory Properties: Cylindrical foam samples (2 mm diameter×1 cm length) are cut, and a 203.20 μm diameter nickel titanium wire is threaded through the length of the sample to serve as a stabilizer. Samples are be crimped to their smallest possible diameter using a stent crimper with heating above the Tg. Initial foam diameter is measured using ImageJ software, and the foams are placed in a water bath at 37° C. Images are taken over 30 minutes, and foam diameter is calculated at each time point using Image)®. Percent recovery versus the original sample diameter and volume expansion is calculated using the resulting measurements.

Figures 5, 6:
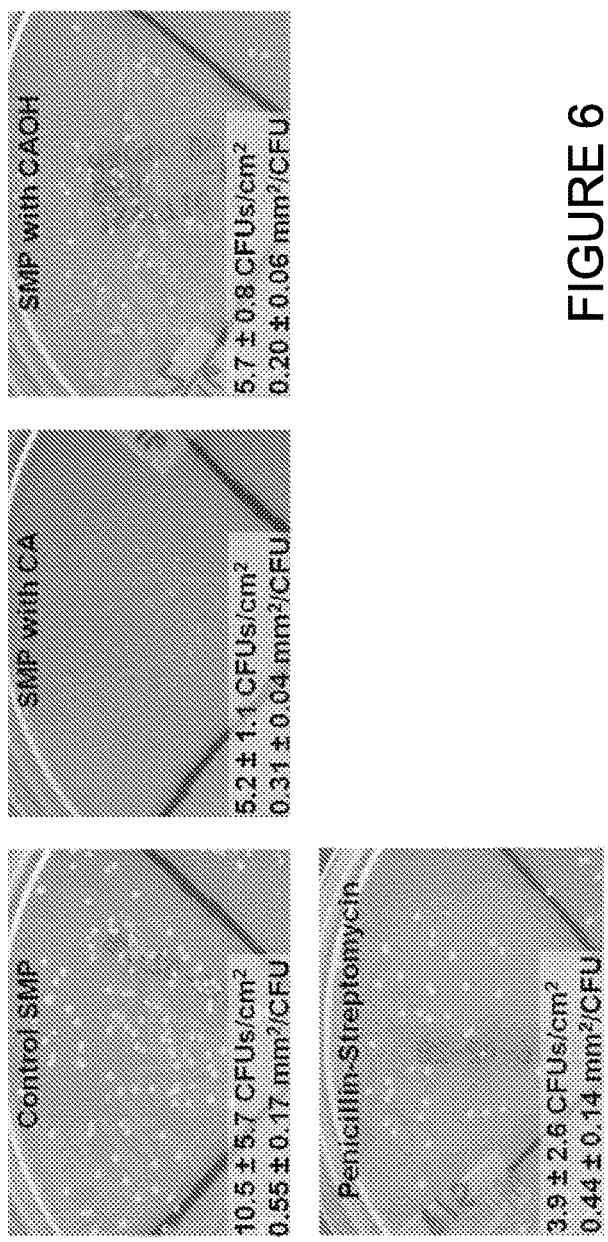
FIG. 5. Thermal and shape memory properties of CA and CAOH containing SMP foams.
FIG. 6. E. coli colony forming units after exposure to control SMPs, SMPs with CA or CAOH, and penicillin-streptomycin (antibiotic control). Both CA and CAOH-containing SMPs reduced the size and number of colonies compared to the control SMP, and both reduced the size of colonies compared to the antibiotic control.
Figure 7:
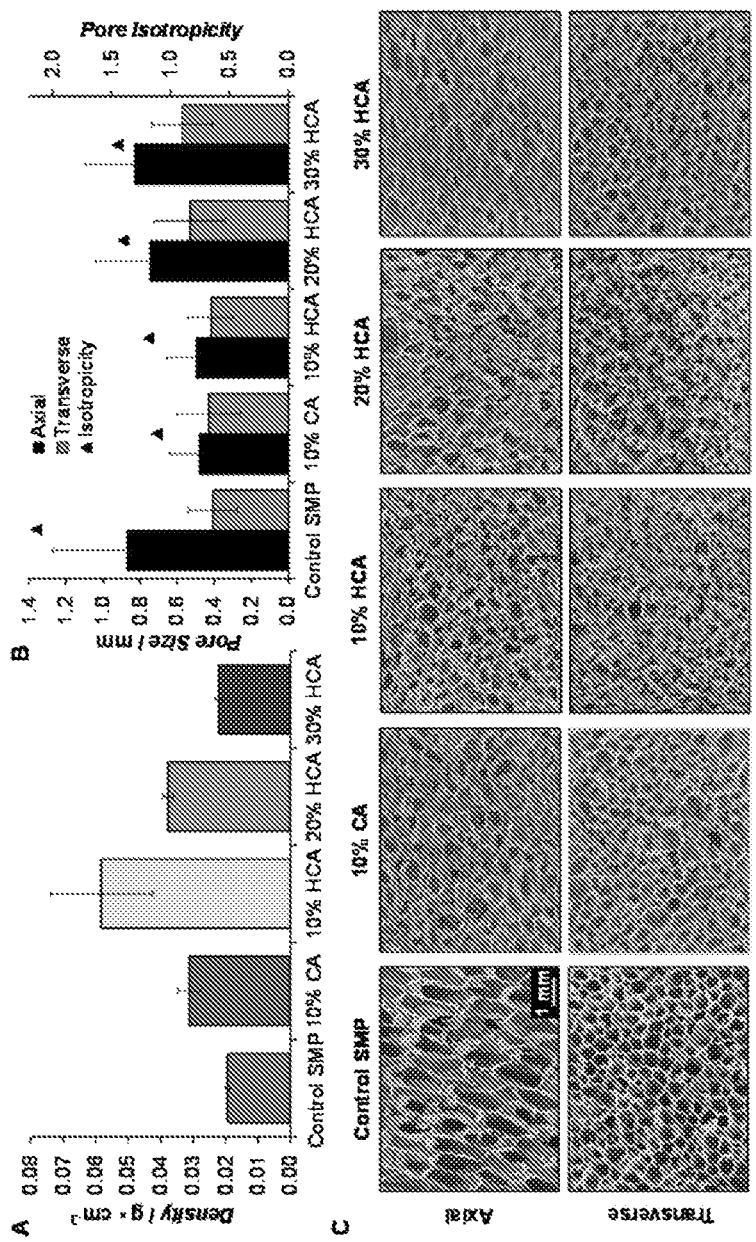
FIG. 7. SMP foam structural properties.

Results: CA and CAOH-containing SMP foams exhibited retained shape memory properties with high volume recovery and volume expansion, FIG. 5.

Study 1.3: Assess antimicrobial properties of PA-containing foams in comparison to clinically available silver-based antimicrobial wound dressings. As an initial indication of the antimicrobial efficacy of PA-containing SMP foams, a series of in vitro studies were conducted with bacteria. Embodiments include formulations with comparable antibacterial properties to those of clinically available antimicrobial oxidized regenerated cellulose hemostats.

Methods: *E. coli* (gram-negative) and *S. epidermidis* (gram-positive) colony forming units (CFUs) are counted after exposure to control foams, PA and PAOH foams, and cellulose hemostats (Surgicel®, Ethicon).

Results: CA and CAOH SMPs greatly inhibit *E. coli* growth (number and size of colonies) relative to control SMPs, FIG. 6.

More Detailed Description of Embodiments

SMP foams embodiments addressed herein provide a biomaterial platform with numerous potential benefits for use as hemostatic dressings. Polyurethane SMPs are fabricated as expanded, open porous foams that can be compressed into a temporary, secondary shape. The compressed shape is retained until the foam is exposed to water and heat, upon which it returns to the original expanded shape. Embodiments are designed to actuate in aqueous conditions between 15 and 45° C. (~40-70° C. in dry conditions), and actuation times are tuned between 30 seconds and 30 minutes. SMP foams demonstrated excellent biocompatibility over 90 and 180 days of implantation in a porcine aneurysm model. Importantly, these foams induce rapid clotting due to their high surface area and thrombogenic material chemistry; in a porcine hind limb vessel, SMP foams promoted arterial hemostasis within 90 seconds of device deployment. SMP foam embodiments have minimal particulate generation, and no undesired downstream clotting has been observed in prior in vivo occlusion studies. Embodiments enable application of a compressed device in a deep, irregularly-shaped bleed site, which rapidly expands upon passive heating to body temperature to space-fill the wound volume and promote hemostasis.

One of the benefits of SMP system embodiments described herein is tunable material chemistry. To enhance hemostatic device performance, antimicrobial agents are introduced into the polymer network. In an embodiment incorporated antimicrobials work in conjunction with oral antibiotics to reduce infection risks and the need for frequent dressing changes. To address concerns about antibiotic-resistant bacterial strains, antimicrobial phenolic acids were utilized to provide a non-drug approach. Bees produce plant-derived phenolic acids in their honey, which protect hives against microbes and viruses. Phenolic acids exhibit broad antimicrobial properties, and have been shown to be effective against multi-drug resistant organisms (MDROs). For example, antibiotic-resistant bacteria that were obtained from hospitals (*Enterobacter aerogenes, Escherichia coli,* and *Staphylococcus aureus*) were susceptible to cinnamic acid. A recent review covers the efficacy of a number of phenolic acids, including cinnamic, gentisic, and benzoic acids, against *Candida* infections (planktonic and biofilms, drug susceptible and drug resistant).

Embodiments incorporate native and modified cinnamic acid (CA) into the SMP system, FIG. 1. The resulting scaffolds were characterized to ensure that the desirable SMP properties were maintained, including density, pore size and structure, thermal properties, shape recovery profiles, and cytocompatibility. An emphasis was placed on design of a SMP foam hemostat that could be stored in extreme battlefield conditions and actuate quickly once exposed to water in blood at body temperature. Antimicrobial efficacy against *Escherichia coli* (*E. coli*) and *Staphylococcus epidermidis* (*Staph. epi.*) was characterized after soaking samples for up to 30 days in saline at body temperature to gain an understanding of initial and sustained antimicrobial effects.

Results and Discussion

Synthesis of CA and HCA-containing SMPs: To enable its incorporation without sacrificing polyurethane network crosslink density, cinnamic acid (CA) was modified via esterification with N,N,N',N'-tetrakis(2-hydroxypropyl) ethylenediamine (HPED) to form a CA-containing triol (HCA). Successful synthesis of HCA was confirmed via Fourier transform infrared (FTIR) and nuclear magnetic resonance (NMR) spectroscopy. In the FTIR spectra, a relative decrease in the hydroxyl groups can be observed at ~3350 $cm^{-1}$, and ester formation was confirmed via a shift in the carbonyl peak from ~1680 to ~1710 $cm^{-1}$, FIG. 2A. NMR showed the presence of esterified CA and HPED, with ~90% functionalization, FIG. 2B.

Upon successful synthesis of HCA, SMP foams were prepared with 10, 20, and 30% HCA (mol % of hydroxyl groups, based off of 3 hydroxyl groups per mole of HCA).

Foams were made with 10, 20 and 30% CA (mol % of hydroxyl groups, based off of 1 hydroxyl group (i.e. carboxylic acid) per mole of CA). The 10% CA foams rose, but 20 and 30% CA, a stable network was not able to form and the foams collapsed. This result was attributed to the termination of the polyurethane network upon reactions between HDI and mono-functional CA. While direct incorporation of CA is faster and simpler, its single functional group is a limitation to its effective use in this SMP system. This result also validates the additional HCA synthesis step, as it allows for more effective incorporation of higher concentrations of CA. The relatively straightforward synthesis method of HCA could be utilized with a range of phenolic acids or other carboxylic acid-containing functional molecules (e.g. drugs, bioactive factors) in some embodiments to impart new properties to the SMP system.

ATR-FTIR spectra were obtained of CA and HCA containing foams, FIG. 2C. There is an additional peak at ~1615 $cm^{-1}$ in all of the CA and HCA foams that is attributed to the C=C groups in the ring structure. The relative absorbance of this peak increases slightly (relative to the urethane peak at ~1680 $cm^{-1}$) with increased HCA concentration. In the 10% CA spectra, the relative absorbance at the 1615 $cm^{-1}$ peak is between that of 20 and 30% HCA, indicating a higher incorporation efficiency with the unmodified CA.

These spectra confirm successful incorporation of CA and HCA into the SMP network. Both routes are viable for effective synthesis of phenolic acid-containing foams.

Structural properties: Foam density and pore sizes were assessed to verify the qualitative observations of successful foam blowing with CA and HCA, FIG. 3. In general, CA and HCA-containing foams retain the ultralow density that is characteristic of this SMP system, FIG. 3A. The 10% HCA foams had a higher density, and there was a trend of decreasing density with increased HCA concentration. These results correspond with pore size measurements, with increasing pore sizes as HCA concentration is increased, FIG. 3B. Qualitatively, 10 and 20% HCA foams have less rounded pores, which further correlates with density measurements, FIG. 3C. Despite these minor differences, overall, CA and HCA foam pore sizes were comparable to those of the control foam, FIG. 3B-C. Improved isotropicity (ratio between pore sizes in the axial and transverse foaming directions) was observed with the CA and HCA foams, indicating that the new monomers aided in constricting the foam rise process to provide more homogeneous pores, FIG. 3B. Overall, these results show that CA and HCA can be incorporated into SMP foams with minimal protocol changes to provide structurally similar materials, further indicating the potential for this method to be used effectively with other functional monomers with similar reactive groups.

Thermal and shape memory properties: For effective field use, SMP foam-based hemostats must retain their compressed geometries at the high temperatures that are reached in desert climates (e.g., up to ~45° C. in Iraq) under dry storage conditions and then rapidly expand upon exposure to water in body temperature blood. As an initial indication of these capabilities, SMP foam glass transition temperatures (Tg's) were measured under dry and wet conditions, FIG. 8A. The 10% CA foam dry Tg was similar to that of the control, and both were below the required 45° C. for field use. CA increases the hydrophobicity of the foams, which generally increases Tg; however, incorporation of the monofunctional group is expected to reduce the overall crosslink density, which had an opposing effect to lower Tg. To increase dry Tg of CA foams to a useful level, overall crosslink density could be increased by utilizing more HPED, or hydrophobicity could be further increased with the introduction of more hydrophobic monomers, such as trimethyl hexamethylene diisocyanate. Incorporation of HCA allowed for crosslink density to be retained while increasing hydrophobicity, resulting in increases in dry Tg with increased HCA content. All HCA-containing foams had dry Tg's at or above 45° C., indicating their potential for use on the battlefield without premature expansion. Additionally, HCA incorporation provides a new tool for tuning SMP foam thermal properties. All CA and HCA foams had wet Tg's below 30° C., allowing for expansion after exposure to body temperature blood, even if the patient is in hypovolemic shock from blood loss and/or subjected to hypothermia.

Figure 8:
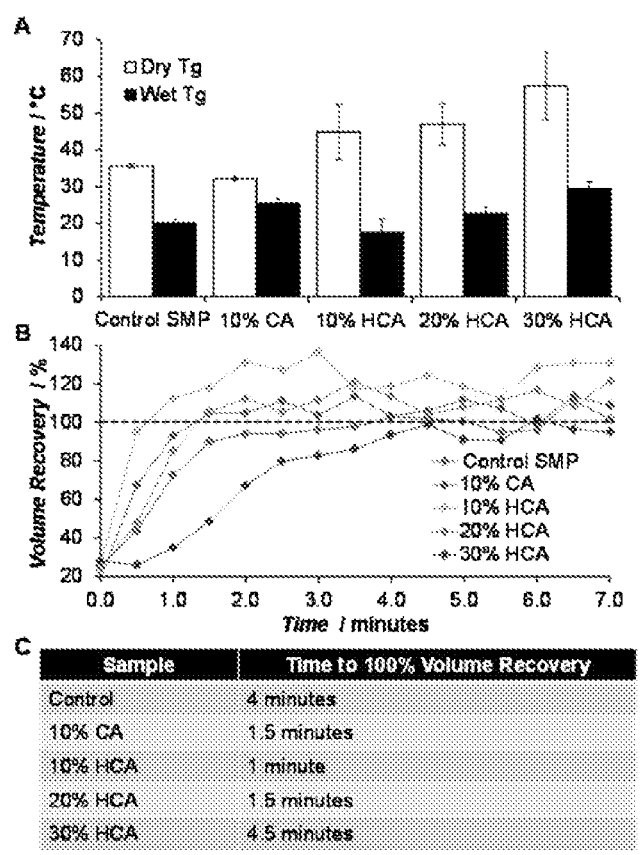
FIG. 8. Thermal and shape memory properties of HCA/CA foams.

To further explore the functional capabilities of CA and HCA SMP foams, their volume expansion profiles were characterized in 37° C. water, FIG. 8B-C. CA foams had more rapid expansion as compared to controls, which is attributed to their theoretically decreased crosslink density due to the incorporation of a monofunctional monomer. Increasing HCA content resulted in slower volume expansion, correlating with increased Tg measurements, and is attributed to increased foam hydrophobicity and backbone stiffness with the introduction of the ring structure in CA. The increase in expansion rate of 10 and 20% HCA foams relative to the control is likely due to network inconsistencies. Although high average functionalization of HCA was achieved, the synthesized monomer is a mix of HPED with varied numbers of tethered CA molecules. The resulting network inhomogeneity can result in more rapid volume expansion, despite increased hydrophobicity. This effect was outweighed with increased HCA content in the 30% HCA foam, where increased hydrophobicity likely had a larger effect on slowing down expansion than network inconsistencies. To address severe bleeds, SMP-based hemostats should achieve full expansion as quickly as possible. Full expansion of 10 and 20% HCA in less than two minutes in combination with their high dry Tg's is highly promising for their potential use as hemostats on the battlefield. The variations in volume expansion rates with increased HCA content further validates the ability to use HCA incorporation as a tool for tuning SMP foam properties.

Figure 9:
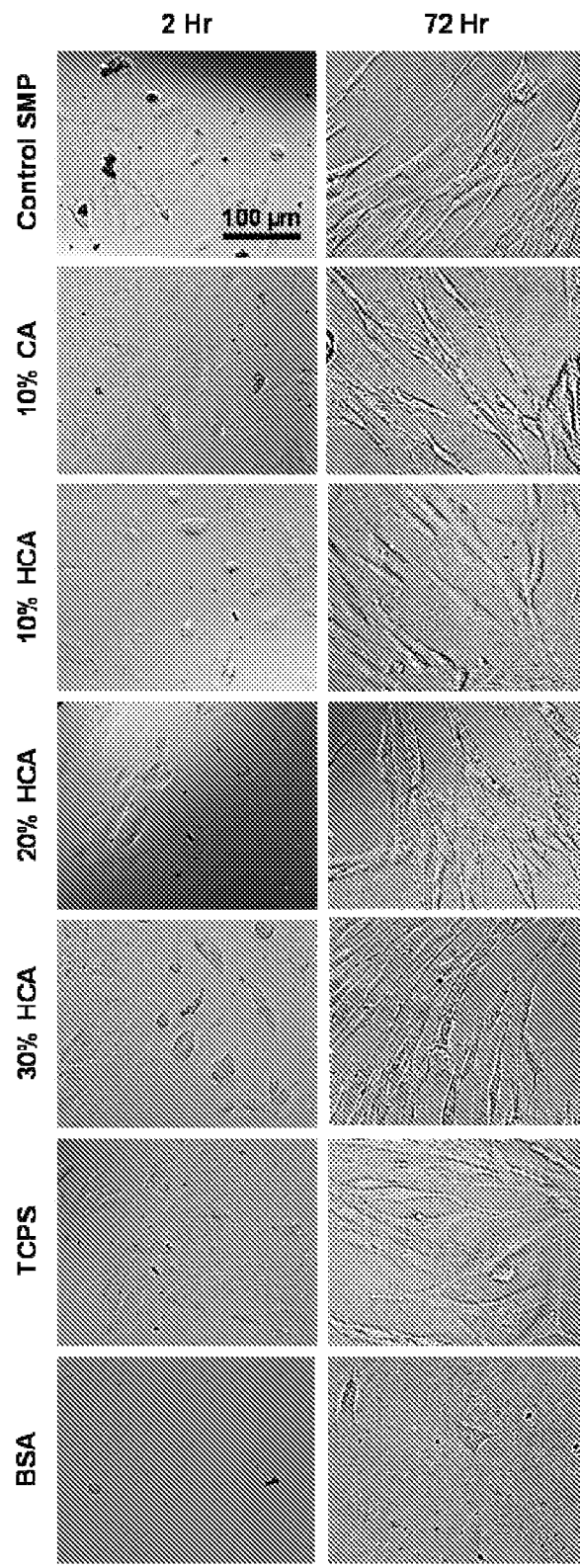
FIG. 9. Representative brightfield images of human dermal fibroblasts after 2 and 72 hr of contact with SMP films. Scale bar applies to all images.

Cytocompatibility: As an initial indication of CA and HCA-containing SMP cytocompatibility, human dermal fibroblasts (HDFs) were indirectly exposed to SMP films, and their morphology, initial attachment, and proliferation were qualitatively assessed, FIG. 9. Initial attachment was similar between wells containing SMP films and the positive control, TCPS. HDFs were evenly attached across the well surfaces and well spread. The negative control, BSA-coated TCPS, had lower attachment and rounded cells. At 72 hours, HDFs had elongated and proliferated in all SMP film-containing wells and the TCPS control with some areas of confluence. The BSA negative control wells still had low attachment numbers and lower spreading after 72 hours. These studies indicate that the modifications did not negatively affect the cytocompatibility of the base SMP formulation, which is a benefit for their use as biomaterial scaffolds.

Figure 10:
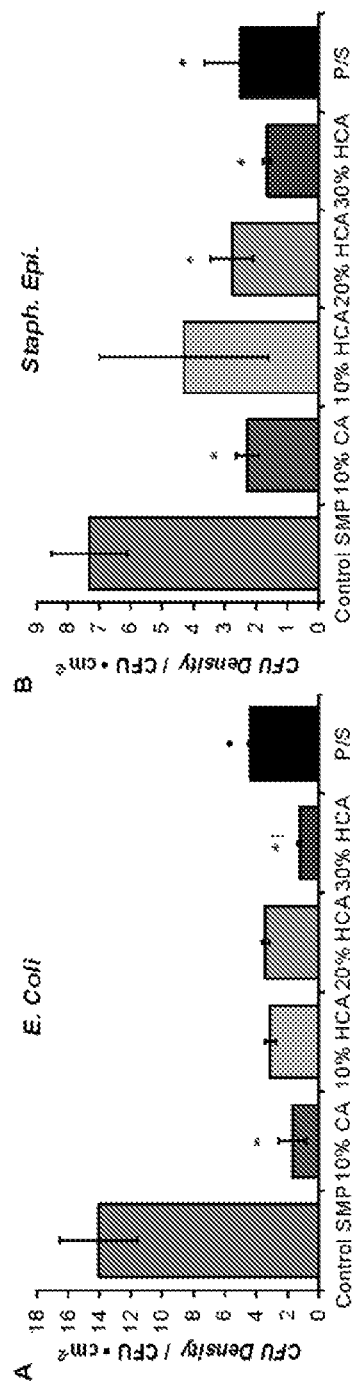
FIG. 10. Colony forming unit (CFU) density of FIG. 10(A) E. coli and FIG. 10(B) Staph. Epi. after exposure to unmodified control, CA, HCA, and penicillin-streptomycin (P/S)-soaked control SMP films. *$p<0.05$ relative to Control. †$p<0.05$ relative to 10% HCA and 20% HCA, •$p<0.05$ relative to all other samples.

Antimicrobial properties: To measure antimicrobial efficacy of CA and HCA following incorporation into SMPs, colony forming unit (CFU) density of *E. coli* (gram negative) and *Staph. epi.* (gram positive) were measured following exposure to SMP films. There were large reductions in *E. coli* CFUs after exposure to CA and HCA-containing films in comparison to unmodified control SMP films. CFU density was at or below that of drug-based (penicillin streptomycin, P/S) controls, FIG. 10A. CFU reductions relative to unmodified control SMP films were significant for 10% CA and 30% HCA films. The improved performance of CA at lower concentrations is likely due to more effective incorporation, as indicated by an increased C=C peak at 1615 cm-1 in the FTIR spectra (FIG. 2C). The increased efficacy of 30% HCA illustrates how antimicrobial properties should increase with increased CA concentration in the films. Similar results were observed with *Staph. epi.*, with significant decreases in CFU density for 10% CA, 20% HCA, and 30% HCA films to levels at or below the drug-based (P/S) control, FIG. 10B. There was a trend of decreasing CFU density with increased HCA concentration. Some phenolic acids have shown increased antimicrobial efficacy after esterification. This result has not been observed with CA. Embodiments include incorporation of phenolic acids that benefit from esterification. Overall, these results demonstrate that the antimicrobial properties of CA are retained following incorporation into SMPs with and without prior modification. The comparable efficacy to P/S is highly promising for potential use of CA or HCA-containing SMPs against drug resistant organisms.

To characterize antimicrobial property retention, CA and HCA containing films were soaked in saline solution at 37°

Figure 11:
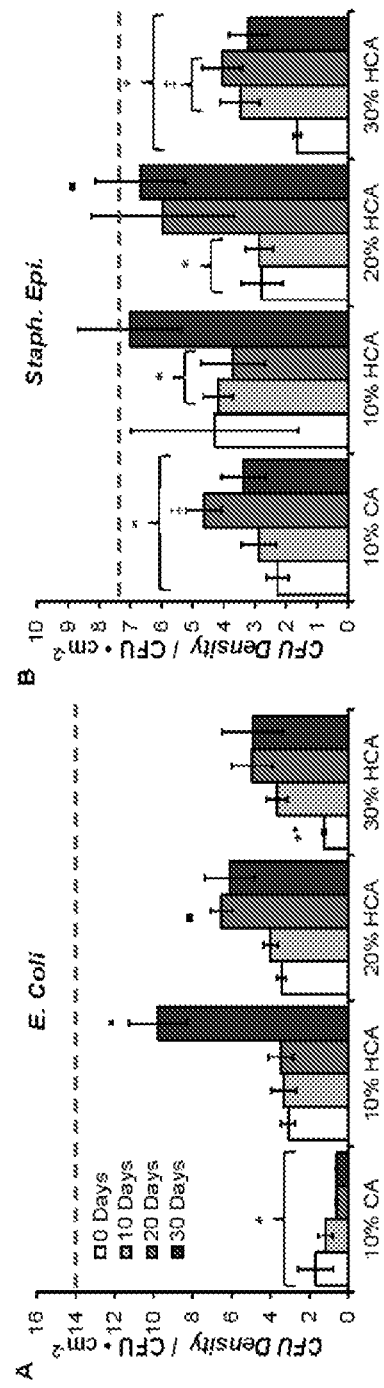
FIG. 11. Colony forming unit (CFU) density of (A) E. coli and (B) Staph. Epi. after exposure to CA and HCA SMP films that had been soaked in phosphate buffered saline at 37° C. for up to 30 days. Red line-Control CFU density. *$p<0.05$ relative to Control. •$p<0.05$ relative to all other time points within formulation, ■$p<0.05$ relative to 10 and 20 day samples within formulation, ‡$p<0.05$ relative to 0 day sample within formulation.

C. for up to 30 days, and *E. coli* and *Staph. epi.* CFU density was measured after exposure to soaked films. All 10% CA films retained significantly lower CFU density compared to the unmodified control SMP for both bacteria types, FIG. 11. The formation of a urethane bond between CA and HDI in the SMP network provides a biostable linkage that is not susceptible to hydrolysis. In an embodiment the majority of the CA was retained in the films throughout the soaking period, providing a sustained antimicrobial effect. The 10% HCA films had comparable CFU densities up to 20 days of soaking, with increases for the 30 day samples that approached the control film value (red dashed line) for both bacteria types. Since HCA is incorporated into the SMP network via an ester linkage, hydrolysis likely caused HCA concentration reductions over time. A similar trend was observed with 20% HCA samples, with increases in the CFU density after exposure to the 20 and 30 day soaked films. Increases in *E. coli* density were lower for 20% HCA at 30 days than those for 10% HCA, indicating a higher retained HCA concentration with increased initial concentration. This trend was further confirmed with 30% HCA films. While CFU density increases were observed between the 0 and 10 day soaked samples, indicating an initial loss of HCA, the CFU density did not dramatically change past 10 days of soaking and never approached that of control films. Thus, even with the hydrolytically-labile linkage, HCA provides a sustained antimicrobial effect in SMPs when incorporated at higher concentrations. These results combined with the favorable thermal and shape memory properties of HCA-containing SMPs indicate their potential for use as antimicrobial hemostats.

Experimental Section

Materials: DC 198, DC 5943, BL-22, T-131, and Enovate® were purchased from Evonik® (Essen, Germany) and used as received. All other chemicals were purchased from Sigma-Aldrich Inc. (St. Louis, Mo.) and used as received.

Phenolic acid monomer synthesis and characterization: N,N,N',N'-tetrakis(2-hydroxypropyl) ethylenediamine (HPED)-cinnamic acid (HCA) was synthesized using an esterification procedure. Cinnamic acid (CA, 1 molar eq.) was added to a round bottom flask and dissolved in chloroform. Then, 4-(dimethylamino) pyridine (DMAP, 0.1 molar eq.) was added to the flask and dissolved. HPED (1 molar eq.) was weighed out in a separate vial, dissolved in chloroform, and added dropwise to the reaction flask. The flask was placed on ice to cool for ~5 minutes. N,N'-dicyclohexyl carbodiimide (DCC, 1.1 molar eq.) was weighed into a separate vial, dissolved in chloroform, and added dropwise to the chilled reaction vessel. The reaction was stirred under nitrogen on ice for 5 minutes and then allowed to proceed at room temperature for 3 hours. After the reaction was complete, the flask was placed at 0° C. for 30 minutes to precipitate dicyclohexyl urea, which was then removed via vacuum filtration. The reaction solution was washed twice with 1 molar eq. of 0.1M HCl and then washed with an aqueous saturated sodium bicarbonate solution. The organic phase was dried over magnesium sulfate and filtered. Then, chloroform was removed using rotary evaporation following drying under vacuum overnight. Fourier transform infrared (FTIR) and nuclear magnetic resonance (NMR) spectroscopy were utilized to confirm synthesis of HCA. 1H NMR (CdCl$_3$): 1.05 ppm (m, HOCHCH$_3$, 9H), 1.2 ppm (m, —OCHCH$_3$, 3H), 2.2-2.6 ppm (m, —CH$_2$—, 12H), 3.6 ppm (m, HOCHCH$_3$, 3H), 5.1 ppm (m, —OCHCH$_3$, 1H), 6.4 ppm (d, —CCH=, 1H), 7.3-7.6 ppm (m, —HC=CHC$_6$H$_5$, 6H).

Shape memory polymer (SMP) foam and film synthesis: An isocyanate (NCO) pre-polymer was synthesized with appropriate molar ratios of HPED, triethanolamine (TEA), HCA or CA, and hexamethylene diisocyanate (HDI), with a 42 mol % hydroxyl (OH) content. A OH mixture was prepared with the remaining molar equivalents of HPED, TEA, and HCA or CA. Foaming agents (catalysts, surfactants, deionized water, and Enovate) were mixed with the NCO-prepolymer and the OH mixture using a speedmixer (FlackTek, Inc., Landrum, S.C.) to induce foam blowing.

The foams were then cured at 50° C. for 5-10 minutes and cooled to room temperature before washing via sonication in isopropyl alcohol (IPA) or reverse osmosis (RO) water for 15 minute cycles. The purified foams were lyophilized to dry.

SMP films were synthesized using the same monomer compositions as the foams, but without surfactants, deionized water, or Enovate®. FIG. 12 shows the SMP compositions that were synthesized and characterized in these studies.

SMP foam density: SMP foam density (n=3) was quantified on foam blocks cut from the top, middle, and bottom section of the foam, according to ASTM standard D-3574. Foam block masses was measured using a gravimetric scale, and length, width, and height values were measured three times per sample using a digital caliper. Density was calculated as mass divided by volume.

SMP foam pore size and structure: To assess pore sizes, thin slices (~1 mm, n=3) were cut from each foam composition in the axial (parallel to foam rise) and transverse (perpendicular to foam rise) foaming directions. Samples were mounted to sample holders with carbon black tape and sputter-coated for 60 seconds at 20 mA (Cressington Sputter Coater®, Ted Pella, Inc. Redding, Calif.). Samples were imaged using a Jeol NeoScope JCM-5000 Scanning Electron Microscope (SEM)® (Nikon Instruments, Inc., Melviille, N.Y.). A line was drawn through the center of each image, and pore size was measured for 5 randomly selected pores on the line using ImageJ software.

SMP foam thermal transitions: The glass transition temperature (Tg) was measured under wet and dry conditions (n=5). To measure dry Tg, foam samples (3-8 mg) were cut and stored with desiccant prior to testing. A Q-200 DSC® (TA Instruments, Inc., New Castle, Del.) was used to obtain the thermogram for each composition using the following program: (1) temperature was decreased to −40° C. at 10° C. min-1 and held isothermally for 2 minutes, (2) temperature was increased to 120° C. at 10° C. min-1 and held isothermally for 2 minutes, (3) temperature was decreased to −40° C. at 10° C. min-1 and held isothermally for 2 minutes, and (4) temperature was increased to 120° C. at 10° C. min-1. The dry Tg was recorded from the second heating cycle using the inflection point of the thermal transition curve. TA Instruments® software (TA Instruments, Inc., New Castle, Del.) was utilized to determine the inflection points.

For wet Tg measurements, foam samples (3-8 mg) were submerged in reverse osmosis (RO) water at 50° C. for 5 minutes to allow full plasticization. The samples were removed from the water, pressed dry with laboratory wipes, weighed, and placed in an aluminum pan with a vented aluminum lid. A Q-200 DSC was used to cool the samples to −40° C. at 10° C. min-1 and hold them isothermally for 2 minutes. The samples were then heated to 80° C. at 10° C. min-1. TA Instruments software was used to generate the thermogram and determine the wet Tg using the average inflection point of the thermal transition.

Various examples at the end of the application address Tg, such as dry Tg and wet Tg. Those terms should be construed in keeping with the immediately preceding two paragraphs (i.e., as used herein dry and wet Tg should be determined using the methods described in the two paragraphs immediately above).

Volume recovery: Cylindrical foam samples (n=3, diameter=4 mm, length=10 mm) were prepared, and a stabilizing 203.20 µm diameter nickel-titanium wire (NDC, Fremont, Calif.) was threaded through the center of each sample along its length. The foam samples were radially crimped to their smallest possible diameter using an ST 150-42 stent crimper (Machine Solutions, Flagstaff, Ariz.). Samples were heated to 100° C., held isothermally for 15 minutes, and programmed to the crimped morphology by cooling to room temperature. Initial foam diameter was measured for each sample using Image J® software (NIH, Bethesda, Md.). The crimped foams were placed in a 37° C. water bath, and images were taken every 30 seconds up to 7 minutes. Foam diameter was measured at each time point at 5 evenly spaced locations along the foam length using Image J®. Percent volume recovery was calculated using Equation 1.

% Volume Recovery=(Recovered diameter/Original diameter)$^2$*100   Eq. 1

Cell interactions: Human dermal fibroblasts (HDFs, Invitrogen, Inc., San Diego, Calif.) were used to assess cell attachment and spreading. In vitro culture was carried out at 37° C./5% $CO_2$ with Medium 105 (Invitrogen) supplemented with low serum growth supplement (Invitrogen) and 1% penicillin-streptomycin (P/S, Gibco). Cells were used at passage 3.

SMP films were cut into 6 mm diameter cylinders and sterilized via incubation in 70% ethanol overnight and subsequent washing in sterile phosphate buffered saline (PBS, 3 washes). As a negative cell attachment control, wells in a 96 well tissue culture polystyrene (TCPS) plate were blocked with a sterile 5% bovine serum albumin (BSA) in PBS. Unmodified TCPS wells served as positive cell attachment controls. HDFs were seeded into wells containing SMP films at 5,000 cells $cm^{-1}$. Seeded cells were cultured at 37° C./5% CO2 for up to 72 hours. Media was changed at 2 and 36 hours. At 2 and 72 hours, brightfield images were obtained to qualitatively assess cell attachment and proliferation. Representative images were obtained using a Nikon Eclipse TE2000-S® with 4 field views per specimen and 3 specimens per sample type.

Antimicrobial properties: To obtain an initial measure of antimicrobial properties, SMP films were cut into 6 mm diameter cylinders. To characterize antimicrobial properties over time, samples were incubated in PBS at 37° C. for 0, 10, 20, or 30 days. Then, films were sterilized as described in the Cell Interactions Section. *Escherichia coli* (*E. coli*) and *Staphylococcus epidermidis* (*Staph. epi.*) were grown overnight in 5 ml of lysogeny broth (LB) at 37° C. Subsequently, 500 µl were taken from each overnight culture and grown in 10 ml of fresh LB to optical density (O.D.) 0.6 (i.e. until bacteria had entered log phase growth). O.D. was measured using a Tecan plate reader. Samples were placed into a sterile 96 well plate, and 100 µl of bacteria solution were pipetted onto the surface of each sample. Control SMP films were soaked in P/S overnight to provide a drug-based antimicrobial control. Samples were incubated with bacteria for 1 hour at 37° C. and then vortexed to dislodge attached bacteria. Bacterial solutions were diluted by 106 in fresh LB and plated onto LB-agar plates overnight at 37° C. Images were obtained of each specimen plating area. Colony forming unit (CFU) density was measured by counting the number of colonies and dividing by the plating area.

Statistics: Data are reported as mean±standard deviation. Student's t-test was used to determine statistical significance, which was accepted at p<0.05.

Embodiments demonstrate successful incorporation of CA, a honey-based phenolic acid, into SMP foams via two routes. The resulting foams retain the desirable porous structure of the control SMP while providing tunable thermal transitions and shape recovery properties that are ideal for their use in hemostats for bleeding control. Namely, CA-based SMPs were designed with high dry Tg's to enable their storage under extreme battlefield conditions and low wet Tg's to enable their rapid shape recovery upon exposure to blood at body temperature. Furthermore, CA-based SMPs have high cytocompatibility while effectively reducing bacterial growth to levels that are comparable to penicillin/streptomycin-based treatments, even after 30 days of storage in saline at body temperature. Overall, embodiments provide a hemostat device that is easy-to-use, biocompatible, and antimicrobial. An additional benefit to phenolic acids is their antioxidant properties; phenolic acids contain hydrogen donating groups that scavenge free radicals and reduce oxidation. This is ideal for SMP foams that are susceptible to oxidative degradation. In other words, pendent phenolic acids may be used in biodurable implants. For example, occlusive foams (e.g., foams for occulting aneurysms) that are biodurable help prevent recanalization—a problem experienced with hydrogel and coil based aneurysm therapies.

Examples of embodiments are described below.

Example 1 includes a shape memory polymer composition with incorporated antimicrobial agents.

Example 2 includes the device of Example 1 wherein the antimicrobial agents are chemically incorporated into the polymer backbone via at least one of: (a) direct reaction between hydroxyls, carboxylic acids, or amines on the antimicrobial agent with the backbone, and (b) reacting a polyurethane monomer or macromer with the antimicrobial agent prior to polymerization to produce pendent antimicrobial species.

Example 3 includes the device of Example 1 wherein the antimicrobial agents are physically incorporated into the polymer.

Example 4 includes the device of Example 1 wherein the antimicrobial agents are utilized to surface treat the polymer.

For instance, rather than modifying the bulk of the polymer, an embodiment functionalizes the surface with antimicrobial agents. This maintains bulk physical/mechanical properties of the polymer, but allows antimicrobial agent incorporation at the surface of the foam.

Example 5 includes the polymer composition of Example 1 wherein: monomers for the SMP foam are selected from a group consisting of hexamethylene diisocyanate (HDI), trimethyl hexamethylene diisocyanate (TMHDI), isophorone diisocyanate (IPDI), triethanolamine (TEA), diethanolamine, butane diol, butyne diol, N,N,N',N' tetrakis (hydroxyl propylene) ethylenediamine (HPED), and the antimicrobial agent is selected from the group consisting of phenolic acids, fluorescent dyes, and silver.

An example network includes a reaction between HPED and an antimicrobial agent with carboxylic acid group to produce a triol with a pendent antimicrobial group. The antimicrobial triol is incorporated into a polyurethane network with HDI, TEA, and HPED to produce a polyurethane with pendent antimicrobial groups throughout the bulk.

Example 6 includes a method for making polymeric foams from Example 1 into a porous structure or foam by one or a combination of processes, including but not limited to, freeze drying, phase separation, emulsion foaming/templating, or physical blowing.

Example 7 includes the polymer of Examples 1 and 6 that can be used in medical device manufacturing and as a medical material, in such devices including but not limited to: subcutaneous implants, aneurysm filling devices, peripheral filling devices, wound dressings, bone grafts, etc.

Example 1a includes a system comprising a thermoset polyurethane shape memory polymer (SMP) foam that includes at least one antimicrobial agent.

Example 2a includes the system of example 1a wherein the SMP foam is chemically bonded to the at least one antimicrobial agent.

Example 3a includes the system of example 2a wherein the at least one antimicrobial agent includes a phenolic acid.

Example 4a includes the system of example 3a wherein the at least one phenolic acid includes at least one of cinnamic acid, benzoic acid, gentisic acid, 4-hydroxy benzoic acid, p-coumaric acid, vanillic acid, syringic acid, protocatechuic acid, gallic acid, ferulic acid, sinapic acid, and caffeic acid.

Example 5a includes the system of example 4a wherein the at least one phenolic acid is a pendent group chemically bonded to a polyurethane polymer chain of the SMP foam.

As used herein a pendant group (sometimes spelled pendent) or side group is a molecule or group of molecules attached to the backbone of a long molecule. Usually, this "long molecule" would be a polymer. Pendant groups are different from pendant chains, as they are neither oligomeric nor polymeric. For example, the phenyl groups are the pendant groups on a polystyrene chain.

Another version of Example 5a includes the system of example 4a wherein the at least one phenolic acid is a pendent structure (one or more molecules that may or may not be in a chain) chemically bonded to a polyurethane polymer chain of the SMP foam.

Example 6a includes the system of example 5a wherein the pendent group is chemically bonded to the polyurethane polymer chain via an ester.

For instance, FIG. 2(B) shows an example of a pendent group (CA) chemically bonded to a polyurethane chain via an ester linkage.

Example 7a includes the system of example 6a wherein the SMP foam has a dry glass transition (Tg) above 40 degrees C. and a wet Tg below 30 degrees C.

Other embodiments may have dry Tg's above 35, 37, 39, 42, 45, 47 or 50 degrees C. and wet Tg's below 34, 32, 28, or 26 degrees C.

Example 8a includes the system of example 2a wherein the at least one antimicrobial agent includes a carboxylic acid group.

Another version of Example 8a includes the system of example 2a wherein the at least one antimicrobial agent includes an amine group.

Another version of Example 8a includes the system of example 2a wherein the at least one antimicrobial agent includes: (a) a first antimicrobial agent that includes an amine group, and (b) a second antimicrobial agent that includes a carboxylic acid group.

Example 9a includes the system of example 1a wherein the SMP foam is physically crosslinked around the at least one antimicrobial agent.

For instance, the agent may not be chemically bonded to the polyurethane chain but the chain may be crosslinked in such manner as to render shape memory properties to the foam and to also physically retain an agent that is not chemically bonded to the chain. As the foam recovers its programmed primary shape (from its compressed secondary shape) the agent may be released.

Embodiments also include SMP foams that BOTH (a) physically crosslink around some antimicrobial agents, and (b) include chemically bonded pendent antimicrobial groups.

Example 10a includes the system of example 1a comprising: a thermoset polyurethane second SMP foam that includes a phenolic acid that is a pendent group chemically bonded to a polyurethane polymer chain of the second SMP foam; and a thermoset polyurethane third SMP foam that includes a phenolic acid that is a pendent group chemically bonded to a polyurethane polymer chain of the third SMP foam; wherein (a) the SMP foam comprises a first foam, and (b) the first, second, and third SMP foams are all enclosed in a sealed kit.

Embodiments come in many varied form factors. Some embodiments include one or more pieces of SMP foam which can be applied independently of one another to a site of bleeding. Other embodiments may tether multiple piece of foam together to help ease their removal. For example, an embodiment includes first and second SMP foams each deployed along a single backbone. The backbone may be metal, cloth, string, suture, or a polymer filament. The sponges may have cloth, dacron, or PTFE pledgets on either side of the SMP foams to help secure the foams to the backbone and to help control any sliding of the foams along the back bone. The pledgets may be secured by simply tying a knot in the backbone adjacent the pledget. Again, this may help a medical practitioner (e.g., a surgeon in an operating room) quickly removing a series of foams that were quickly placed in a wound in traumatic/urgent conditions (e.g., a medic treating a soldier in the field or an emergency medical technician treating a gunshot wound in the community). Foams may couple to gauze. The gauze may be a strip of gauze to which the foams are coupled. However, the gauze may be a gauze pouch that includes multiple foams and the entire pouch is placed in a wound (and then easily recovered at a later time considering all the foams are retained within a single pouch). The foam pieces themselves may be formed as pellets (regularly or irregularly shaped, one or many, cylindrical, conical, and/or planar sheets) which may be placed into a wound and those pellets may or may not be coupled to one another. Other embodiments may couple one or more foams to a backbone, such as a Nitinol coil, and then deployed into an aneurysm, peripheral vessel that is desired to be occluded, in a void of a septal wall, and the like. Other embodiments include simply deploying a free foam from a catheter to an internal bleed site. Other embodiments include a single large foam that can be independently placed at any bleeding site or any site with liquids a user wishes to control (e.g., remove).

Example 11a includes a method comprising: reacting a first polyol portion with an antimicrobial agent to form a first reaction product; reacting a first portion of the first reaction product with a second polyol portion and an isocyanate to form a second reaction product; reacting the second reaction product with a second portion of the first reaction product and a third polyol portion to form a third reaction product; mixing the third reaction product with a blowing agent to form a shape memory polymer (SMP) foam; wherein the SMP is a thermoset polyurethane SMP foam.

For example, see FIG. 1 (Route B) which includes reacting a first polyol portion (HPED from line 1 of Route B) with an antimicrobial agent (CA) to form a first reaction product (HCA from line of Route B); reacting a first portion of the first reaction product (HCA from line 2 of Route B) with a second polyol portion (HPED and/or TEA from line 2 of Route B) and an isocyanate (HDI from line 2 of Route B) to form a second reaction product (prepolymer from line 2 of Route B); reacting the second reaction product (prepolymer) with a second portion of the first reaction product (HCA from line 3 of Route B) and a third polyol portion (HPED and/or TEA from line 3 of Route B) to form a third reaction product; mixing the third reaction product with a blowing agent to form a shape memory polymer (SMP) foam; wherein the SMP is a thermoset polyurethane SMP foam.

Another version of Example 11a includes reacting a first polyol portion (HPED or some other polyol) with an antimicrobial agent (CA or some other agent) to form an antimicrobial monomer as the first reaction product; reacting a first portion of the first reaction product with a second polyol portion (HPED and/or TEA and or some other polyol) and an isocyanate (HDI or some other isocyanate) to form a second reaction product (prepolymer); reacting the second reaction product (prepolymer) with a second portion of the first reaction product and a third polyol portion (HPED and/or TEA or some other polyol) and, in response thereto, forming a shape memory polymer (SMP) foam; wherein the SMP is a thermoset polyurethane SMP foam.

In an embodiment the "side A" portion of the reaction includes hydroxyl components, such as HPED, TEA, HCA, CA, and combinations thereof in addition to water. The "side B" portion of the reaction includes the prepolymer described above (where the prepolymer contains unreacted isocyanates). The side A and side B are mixed and a foam blowing reaction occurs.

By saying above a first polyol portion and a second polyol portion these portions may be two portions of a single polyol or may include two (or more) different polyols from one another.

Example 12a includes the method of example 11a wherein the at least one antimicrobial agent includes a phenolic acid.

Example 13a includes the method of example 12a wherein the phenolic acid includes at least one of cinnamic acid, benzoic acid, gentisic acid, 4-hydroxy benzoic acid, p-coumaric acid, vanillic acid, syringic acid, protocatechuic acid, gallic acid, ferulic acid, sinapic acid, and caffeic acid.

Example 14a includes the method of example 12a wherein reacting a first polyol portion with an antimicrobial agent to form a first reaction product comprises esterification of the antimicrobial agent.

For example, line 1 of Route B of FIG. 1 depicts one example of esterification.

Example 15a includes the method of example 11a wherein the first reaction product comprises a triol.

Example 16a includes the method of example 15a wherein: at least one of the first, second, and third polyol portions includes at least one of triethanolamine (TEA), diethanolamine, butane diol, butyne diol, and N,N,N',N' tetrakis (hydroxyl propylene) ethylenediamine (HPED); and the isocyanate includes at least one of hexamethylene diisocyanate (HDI), trimethyl hexamethylene diisocyanate (TMHDI), and isophorone diisocyanate (IPDI).

Example 17a includes the method of example 16a wherein the antimicrobial agent includes at least one of a phenolic acid, a fluorescent dye, and silver.

Example 18a includes the method of example 17a wherein the antimicrobial agent includes a carboxylic acid group.

Example 19a includes the method of example 18a wherein the antimicrobial agent includes at least one phenolic acid that is a pendent group chemically bonded to a polyurethane polymer chain of the SMP foam.

Example 20a includes the method of example 19a wherein the pendent group is chemically bonded to the polyurethane polymer chain via an ester.

Example 21 includes the method of example 11a wherein the second reaction product is a prepolymer formed before polymerization of the SMP foam.

As used herein, the term "pre-polymer" refers to a monomer or system of monomers that have been reacted to an intermediate molecular mass state. This material is capable of further polymerization by reactive groups to a fully cured high molecular weight state. As such, mixtures of reactive polymers with un-reacted monomers may also be referred to as pre-polymers. The term "pre-polymer" and "polymer precursor" may be interchanged.

In an embodiment the prepolymer includes unreacted isocyanates.

Example 22 includes a method comprising: reacting a first polyol portion with a first antimicrobial agent portion and an isocyanate to form a first reaction product; reacting the reaction product with a second polyol portion and a second antimicrobial agent portion to form a second reaction product; mixing the second reaction product with a blowing agent to form a shape memory polymer (SMP) foam; wherein the SMP is a thermoset polyurethane SMP foam; wherein the first reaction product is a prepolymer formed before polymerization of the SMP foam.

For example, Route A of FIG. 1 includes reacting a first polyol portion (HPED and/or TEA of line 1 of Route A) with a first antimicrobial agent portion (e.g., CA of line 1 of Route A) and an isocyanate (e.g., HDI of line 1 of Route A) to form a first reaction product (e.g., prepolymer of line 1 of Route A); reacting the first reaction product with a second polyol portion (HPED and/or TEA of line 2 of Route A) and a second antimicrobial agent portion (e.g., CA of line 2 of Route A) to form a second reaction product; mixing the second reaction product with a blowing agent to form a shape memory polymer (SMP) foam; wherein the SMP is a thermoset polyurethane SMP foam; wherein the first reaction product is a prepolymer formed before polymerization of the SMP foam.

Another version of Example 22 includes For example, Route A of FIG. 1 includes reacting a first polyol portion (HPED and/or TEA or some other polyol) with a first antimicrobial agent portion (e.g., CA and/or some other antimicrobial agent) and an isocyanate (e.g., HDI or some other isocyanate) to form a first reaction product (e.g., prepolymer); reacting the first reaction product with a second polyol portion (HPED and/or TEA or some other polyol) and a second antimicrobial agent portion (e.g., CA and/or some other antimicrobial agent); forming a shape memory polymer (SMP) foam in response thereto; wherein the SMP is a thermoset polyurethane SMP foam; wherein the first reaction product is a prepolymer formed before polymerization of the SMP foam.

Example 23 includes the method of example 22a wherein the antimicrobial agent includes at least one phenolic acid that forms a pendent group chemically bonded to a polyurethane polymer chain of the SMP foam.

Thus, despite a number of clinically available hemostats, uncontrolled bleeding is the primary cause of trauma related death. Shape memory polymer (SMP) foams have a number of desirable properties for use as hemostats, including shape recovery to enable delivery into bleed sites, biocompatibility, and rapid blood clotting. To expand upon this material system, the current work aims to incorporate phenolic acids, which are honey-based antimicrobial agents, into SMP foams. Applicant showed that cinnamic acid (CA) can be utilized as a monomer in SMP synthesis to provide foams with comparable pore structure and retained cytocompatibility. The addition of CA enabled tuning of thermal and shape memory properties within clinically relevant ranges. Furthermore, the modified foams demonstrated initial and sustained antimicrobial effects against gram-positive and gram-negative bacteria. These multi-functional scaffolds demonstrate potential for use as hemostats to improve upon current hemorrhage treatments and provide a new tool in tuning the biological and material properties of SMP foams.

The foregoing description of the embodiments of the invention has been presented for the purposes of illustration and description. It is not intended to be exhaustive or to limit the invention to the precise forms disclosed. Persons skilled in the relevant art can appreciate that many modifications and variations are possible in light of the above teaching. Persons skilled in the art will recognize various equivalent combinations and substitutions for various components shown in the Figures. It is therefore intended that the scope of the invention be limited not by this detailed description, but rather by the claims appended hereto.

What is claimed is:

1. A system comprising:
   a thermoset polyurethane shape memory polymer (SMP) foam that includes at least one antimicrobial agent;
   wherein the at least one antimicrobial agent includes a phenolic acid, and the SMP foam has a dry glass transition temperature ($T_g$) above 40 degrees C. and a wet $T_g$ below 34 degrees C.;
   wherein the SMP foam includes a reaction product of hexamethylene diisocyanate (HDI) with one or more of trimethanolamine (TEA), N,N,N',N' tetrakis (hydroxyl propylene) ethylenediamine (HPED), or combinations thereof;
   wherein the phenolic acid is a pendant group chemically bonded, via an ester, to a polyurethane polymer chain of the SMP foam; and
   wherein the phenolic acid includes one or more of benzoic acid, gentisic acid, 4-hydroxy benzoic acid, p-coumaric acid, vanillic acid, syringic acid, protocatechuic acid, gallic acid, ferulic acid, sinapic acid, caffeic acid, or combinations thereof.

2. The system of claim 1 wherein the SMP foam is physically cross-linked around the at least one antimicrobial agent.

3. The system of claim 1 comprising:
   a thermoset polyurethane second SMP foam that includes a phenolic acid that is a pendent group chemically bonded to a polyurethane polymer chain of the second SMP foam; and
   a thermoset polyurethane third SMP foam that includes a phenolic acid that is a pendent group chemically bonded to a polyurethane polymer chain of the third SMP foam;
   wherein (a) the SMP foam comprises a first foam, and (b) the first, second, and third SMP foams are all enclosed in a sealed kit.

4. The system of claim 1, wherein the wet $T_g$ is below 30 degrees C.

* * * * *